United States Patent [19]

Freundlich et al.

[11] Patent Number: 5,067,949
[45] Date of Patent: Nov. 26, 1991

[54] INSTRUMENT FOR UNSHEATHING, RESHEATHING AND DISPOSING OF A MEDICAL SYRINGE NEEDLE

[76] Inventors: Lawrence F. Freundlich, 923 First St., New Hyde Park, N.Y. 11040; Arthur Karmen, 110 Colonial Pkwy., Manhasset, N.Y. 11030

[21] Appl. No.: 512,466

[22] Filed: Apr. 23, 1990

[51] Int. Cl.$^5$ .............................................. A61M 5/32
[52] U.S. Cl. ................................. 604/263; 604/110; 206/366; 128/917
[58] Field of Search ............... 604/110, 187, 192, 263; 206/365, 366; 128/917

[56] References Cited

U.S. PATENT DOCUMENTS

| | | | |
|---|---|---|---|
| 2,617,719 | 1/1989 | Christphe-Debrium | 604/263 |
| 4,737,149 | 4/1988 | Gillilan | 604/192 |
| 4,738,362 | 4/1988 | Burns et al. | 206/366 |
| 4,801,013 | 1/1989 | Bruno | 206/366 |
| 4,867,309 | 9/1989 | Germaine | 206/366 |
| 4,875,583 | 10/1989 | Nosanchuk | 206/365 |
| 4,922,597 | 5/1990 | Ikeda et al. | 29/240 |
| 4,955,865 | 9/1990 | Steiner et al. | 604/192 |
| 4,981,476 | 1/1991 | Aichlmayr et al. | 604/192 |
| 4,986,811 | 1/1991 | Thead et al. | 604/110 |
| 4,989,307 | 2/1991 | Sharpe et al. | 29/240 |
| 5,024,666 | 6/1991 | Pituch | 604/263 |
| 5,031,767 | 7/1991 | Poruno | 206/370 |

FOREIGN PATENT DOCUMENTS

| | | | |
|---|---|---|---|
| 2601512 | 3/1977 | Fed. Rep. of Germany | 604/110 |
| 2586566 | 3/1987 | France | 604/192 |
| 2603872 | 3/1988 | France | 206/366 |
| 2602340 | 3/1989 | France | 604/263 |
| 2215215 | 9/1989 | United Kingdom | 604/263 |
| 9000074 | 1/1990 | World Int. Prop. O. | 604/110 |

*Primary Examiner*—C. Fred Rosenbaum
*Assistant Examiner*—Mark O. Polutta
*Attorney, Agent, or Firm*—Nicholas J. Garofalo

[57] ABSTRACT

An instrument for protecting the user of a medical syringe from being pricked by its needle when unsheathing or resheathing the needle. The instrument has an upper member releasably mounted atop a disposable container. A vertical passage through the upper member empties through a hole into the container. The passage has a coned entry mouth enabling the user to guide the sheathed needle end of a syringe into the passage. A cam in the upper member is pivotable to hold the sheathed needle in the passage, so that the user may pull on the syringe and separate its needle end from the sheath; or later, the user may reinsert the used needle end of the syringe into the cammed sheath and, upon twisting the syringe, separate it from the needle to allow the separated resheathed needle to drop into the container following release of the cammed condition; or the user may in the latter case instead of twisting the syringe simply release the cammed condition to allow the resheathed needle attached to the syringe to be withdrawn from the instrument.

5 Claims, 1 Drawing Sheet

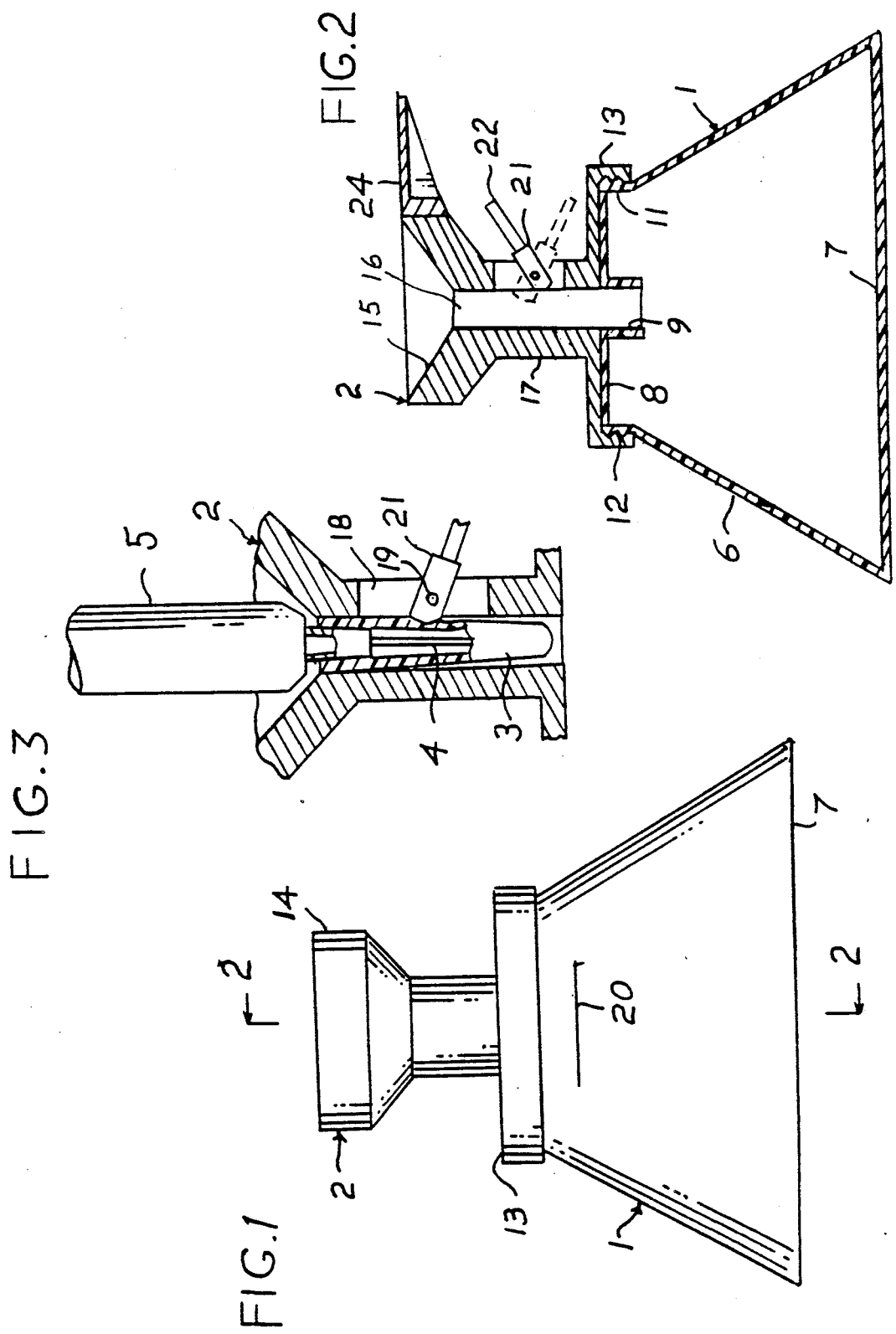

INSTRUMENT FOR UNSHEATHING, RESHEATHING AND DISPOSING OF A MEDICAL SYRINGE NEEDLE

BACKGROUND OF THE INVENTION

This invention is directed to an instrument for protecting the user of a medical syringe from the hazards of needle pricking and possible contamination often occurring when he is unsheathing, resheathing, and disposing of the syringe needle.

A medical syringe is used for injecting liquids into or withdrawing them from the body. Often during its use the user is accidentally pricked by its needle. He may then be subjected to infection, especially when the syringe has been applied to a person having a communicable disease. One does not always know whether the person is diseased until after the liquid has been examined. Owing to the facts that such dangerous infectious diseases as hepatitis and AIDS are transmitted by blood and other body fluids, the consequences of accidental pricking of the user by the needle can be devastating. Such accidental pricking usually occurs when the user is unsheathing, resheathing or disposing of the needle of the syringe.

The conventional medical syringe has a tubular body provided at its bottom with a tip, known as a luer tip. The conventional needle has a plastic hub at its rear which has a connection with the tip requiring the application of a twisting force to effect a separation of the one from the other. Before being put to use the needle is protectively covered by a tubular sheath. The sheath has a splined engagement with the hub of the needle and may be removed by pulling it away from the hub. And the sheath with the needle attached may be separated from the syringe by manually twisting the syringe relative to the needle. Although unwise and not recommended, occasionally after use the needle is resheathed as a protective measure for its disposal. It is during these actions of the user in unsheathing, resheathing, and disposing of the needle that accidental pricking of the user occurs.

Accordingly, a general object of this invention is to provide an instrument which can be employed by the user of a syringe to enable him to protectively unsheath, resheath and dispose of the needle of a syringe without danger of his being pricked by the needle.

A more particular object of the invention is to provide an instrument in which the sheathed end of a syringe may be inserted and clamped in place so as to enable the user to apply a pulling force on the syringe to effect unsheathing of the needle from the sheath, or to apply a twisting force to the syringe to effect a separation of the needle with the sheath attached from the syringe; and which instrument includes a container at its bottom into which the sheath and needle when removed will drop for disposal upon a releasing of the clamped condition of the sheath.

A further object of the invention is to provide an inexpensive instrument of simple construction which is practical and efficient for the foregoing purposes.

The invention further lies in the particular structure and arrangement of its components as well as in their mode of association with one another to effect the objects and advantages intended herein.

BRIEF SUMMARY OF THE INVENTION

The invention is an instrument having an upper member with a vertical passage through it opening into a lower disposable container member. The container has a screw connection with the upper member to allow removal of the one from the other. The passage is designed with a coned mouth enabling a guided entry of the sheathed needle end of a syringe into the passage. A manipulative cam in the passage is operable to hold the entered sheathed needle in place to permit the sheath or the sheath together with the needle to be separated from the syringe. The syringe is of conventional make. The needle has a hub removably engaged by a twist connection with the syringe; and the sheath is removably splined to the hub. Accordingly, when the sheath is held in the passage of the instrument by the cam, a manual pulling action applied to the syringe will separate the sheath from the needle; and, when the syringe is manually twisted relative to the cammed sheath, the sheath together with the needle on which it is mounted will be separated from the syringe. When the cammed condition is manually released, the separated items will drop through the passage of the instrument into the disposable container below. When the container is filled to a guide line marked upon it, it should be unscrewed from the upper member and discarded with its contents. Except for a small entry hole for receiving the separated items, the container is otherwise closed as a safeguard against spilling of its contents. Further, the container is of a material through which a view may be had of its contents; and it is formed of an unbreakable material to avoid breakage of the container and spilling of its contents in the event it is dropped.

The foregoing structure of the invention, its features and advantages will become increasingly apparent as this specification unfolds in greater detail and as it is read in conjunction with the accompanying drawing wherein an embodiment of the invention is illustrated. It is to be expressly understood, however, that the drawing is for purposes of illustration and description, and it is not to be construed as defining the limits of the invention.

BRIEF DESCRIPTION OF THE DRAWING

In the accompanying drawing:

FIG. 1 is an elevational view of an instrument embodying the invention;

FIG. 2 is a section on line 2—2 of FIG. 1, and shows in broken line the camming element in its camming position; and FIG. 3 is a view on an enlarged scale showing a conventional medical syringe with needle and sheath attached, the hub of the needle being shown partly in section, the sheath being shown partly in section and the sheathed end of the syringe being shown inserted in the upper member of the instrument in cammed condition.

DETAILED DESCRIPTION OF THE INVENTION

The invention will now be described with reference to the accompanying drawing and in such concise manner as to enable persons having ordinary skill in the art to make and use the same.

The instrument embodying the invention, as illustrated in the drawing, includes a lower member or container 1, atop which is mounted an upper member 2. The upper member is structured to enable the user to remove the sheath 3 and needle 4 from a conventional medical syringe 5 and causing both to drop into the container below without the user at anytime manually contacting either the sheath or the needle.

The container has a coned body 6 which is truncated at its top and has a broad base 7. The coned body and broad base provide substantial stability to the instrument, whereby it is difficult for the instrument to be accidentally tipped over. A transversely extending cover or wall 8, with the exception of a small center hole 9 in the wall, closes the top end of the container, whereby the contents of the container are virtually sealed in and blocked against escape. The container has a short annular neck 11 at its top, which is threaded about its periphery, as at 12, for screw engagement with a cap 13 defined by a complementary base end of the upper member 2.

The upper member has a head portion 14 provided with a coned entry mouth or cavity 15 which opens at its bottom into a narrow vertical cylindrical passage 16. The latter passage extends down through a neck section 17 of the upper member and opens through the cap 13 at the base of the upper member. The open bottom end of passage 16 registers with a hole 9 that opens into the container 1 below. A slot 18 opens through the side wall of the neck section into the passage 16; and pivoted between the walls of the slot on a pin 19 is a cam element 21 having an externally projecting handle 22. When the handle is manually actuated clockwise, (broken line in FIG. 2), a cam end surface of the cam element is carried into the passage 16; and when the handle is actuated counter-clockwise, the cam end surface is carried clear of the passage. The passage is of a diameter sufficient to receive with slight clearance the sheathed needles of conventional diameters.

In making use of the instrument, when the sheath is to be removed from the needle, the sheathed end of the syringe will be guided down the coned cavity 15 into the passage 16. The cam element 21 will then be pivoted clockwise into cammed contact with the sheath to hold it fast, as illustrated in FIG. 3. The user will then pull outwardly on the syringe to draw the needle out of the sheath. He may then use the syringe to inject the needle into a patient.

After the needle has been used and it is desired to discard it, the user, while holding the syringe, will then guide the unsheathed needle down the coned cavity and into the sheath that is still being held fast in the passage 16 by the cam element. Next, the user will manually twist the syringe relative to the sheathed needle to effect separation of the needle from the syringe. And finally, as the user pivotally releases the cam element from the sheathed needle, the needle and sheath as a unit will drop out of the passage and through the hole 9 into the container below. If, instead, the user merely chooses to resheath the needle and remove the syringe with the needle attached from the passage 16, he will after inserting the needle into the sheath release the cam. He may then withdraw the syringe and the sheathed needle as a unit from the passage.

The container is formed of material, which may be translucent or transparent, so as to enable the user to visually note when it is filled for disposal. A colored mark 20 on the container serves to indicate to the user the point at which the container is to be considered filled. When the container is filled, it may be manually unscrewed from the upper member and discarded. The material of which the container is formed is of an unbreakable nature, such as plastic, so that if the instrument is accidentally dropped, the container will not break open and spill its contents.

A hand guard 24 mounted to the upper member overhangs the cam handle. It serves as a further protective measure to guard against contact of the user's hand with the needle of the syringe when he is entering the needle end of the syringe into the upper member.

While an embodiment of the invention has been illustrated and described in detail, it is to be expressly understood that the invention is not limited thereto. Various changes in form, design or arrangement may be made in its components without departing from the spirit and scope of the invention. It is our intent, therefore, to claim the invention not only as shown and described, but also in all such forms and modifications or equivalents thereof as might be construed to be within the spirit of the invention when considered in the light of the specification, the drawing and the appended claims.

What is claimed is:

1. An instrument for removing sheathed needles comprising: a container lower member having a broad base and a coned body with a threaded truncated open top end; and an upper member having an annular shoulder at its bottom end defining a threaded cap threadedly engaged onto the top end of the container member, the upper member having a neck portion extending axially upward from the shoulder and terminating in a head provided with a coned cavity, the coned cavity merging at its bottom with a narrow passage extending axially down through the neck portion and communicating with the open top end of the container member, the neck portion having a vertically extending slot through its side wall opening into the narrow passage, a cam element pivotably mounted between opposed walls of the slot, the cam element having a handle portion extending externally of the slot and having at its opposite end a cam surface which cam surface is movable into the narrow passage as the cam element is pivoted by its handle in one direction and is movable out of the narrow passage as the cam element is pivoted by its handle in an opposite direction, the coned cavity serving as a guide to manual entry of a sheathed end of a medical syringe down into the narrow passage, and the cam element being adapted upon being pivoted in the one direction to press its cam surface against the sheathed end of the syringe to allow the syringe to be manually drawn free of its sheathed end, and the cam element being adapted upon being pivoted by its handle in the opposite direction to free the cam surface from the sheathed end to allow the separated sheathed end to drop down the narrow passage into the container below.

2. An instrument for removing sheathed needles as in claim 1, wherein a hand guard extends radially from the surface of the head, the guard serving as a rest for steadying the hand of the user when entering the sheathed end of the syringe down the coned cavity and into the narrow passage.

3. An instrument for holding a sheathed end of a medical syringe to enable separation of the sheathed end from the syringe and for effecting its disposal subsequent to its separation, the instrument comprising: a disposable container 1 having a broad base and an open threaded top end; and an upper member having a peripheral shoulder about its bottom defining a threaded cap threadedly engaged over the open threaded top of the container, a neck portion extending axially upward from the shoulder and terminating in a head at its top end, the head having a coned cavity merging at its bottom with a vertical passage extending down through the neck portion and opening into the container, the coned cavity serving as a guide to manual entry of the sheathed end of a medical syringe into the vertical passage, the neck portion having a vertical slot through a side thereof opening into the vertical passage, and a manually operable cam element pivotably mounted between opposed walls of the slot adapted upon being pivoted in one direction to enter a cam end thereof into pressed engagement with the sheathed end of a medical syringe entered into the passage whereby the sheathed end is subject to separation from the syringe upon manual actuation of the syringe in a predetermined direction, and the cam element is adapted upon being pivoted in an opposite direction to move its cam end clear of the separated sheathed end whereby the sheathed end may drop down the passage into the disposable container below.

4. An instrument for removing sheathed needles comprising a container lower member having a broad base and an open threaded top end; and an upper member having an annular shoulder at its bottom defining a threaded cap threadedly engaged over the threaded top end of the container, the upper member having a neck portion extending axially upward from the shoulder and terminating in a head at its top, the head having a coned cavity merging at its bottom with a vertical passage extending down through the neck portion and communicating with the open top of the container, the neck portion having a vertical slot through a side thereof opening into the vertical passage, and a manually operable cam element pivotably mounted between opposed walls of the slot adapted upon being pivoted in one direction to enter and restrict the vertical passage and adapted upon being pivoted in an opposite direction to clear the vertical passage.

5. An instrument for removing sheathed needles as in claim 4, wherein the container has a coned body with a truncated open top end.

* * * * *